United States Patent [19]

Bowker

[11] Plant 4,957

[45] Nov. 23, 1982

[54] AVOCADO TREE

[75] Inventor: John K. Bowker, 16290 Palomino Dr., Porterville, Calif. 93257

[73] Assignees: John King Bowker; Victor Vane Bowker, Jr.; Susan Elizabeth Buckley, all of Porterville, Calif.

[21] Appl. No.: 233,255

[22] Filed: Feb. 10, 1981

[51] Int. Cl.[3] ..... A01H 5/03

[52] U.S. Cl. ..... Plt./44

[58] Field of Search ..... Plt./44

*Primary Examiner*—Robert E. Bagwill
*Attorney, Agent, or Firm*—Lyon & Lyon

[57] ABSTRACT

An avocado tree having limited height and limited spread, and an extended harvest period wherein the fruits may be left on the tree to increase in size and oil content.

4 Drawing Figures

BACKGROUND OF THE INVENTION

This invention relates to a new and distinct variety of avocado tree having certain highly desirable characteristics. As compared with those varieties well known in the section where the new variety originated, it has a longer period during which the fruit can be left on the tree for picking and still retain a high degree of edibility and quality, and also has limited height and limited spreading characteristics compared to other varieties in the region.

The new avocado tree originated in the groves of Bowker & Co., Inc., in Porterville, Calif., from a sporting budding of Harms on Topa Topa root stock. The tree was first discovered by John K. Bowker in 1970, but the new and distinct characteristics were not appreciated until 1979. Thereafter, the new variety was successfully asexually reproduced by Victor V. Bowker and John K. Bowker by budding on several Topa Topa root stock. This resulted in several progeny trees which have continually displayed the growth and fruit characteristics typical of that found on the parent tree. The new avocado tree is particularly suited to warm, inland valley regions.

The fruit of the present variety has an exterior skin which is similar to a Harms variety but is otherwise distinguishable from that variety. The fruit is larger than that of a Harms, and the skin of the fruit is thicker than that of a Harms which, in turn, provides for improved shelf life and shipping qualities. As indicated earlier, the harvest period for the fruit of the present variety is longer than that of a Harms. Further distinguishing the present variety from other varieties common to the section where it originated, the fruit has a thicker skin than that of Fuerte, Zutano and Bacon varieties and is more ovate in shape.

Figure 1:
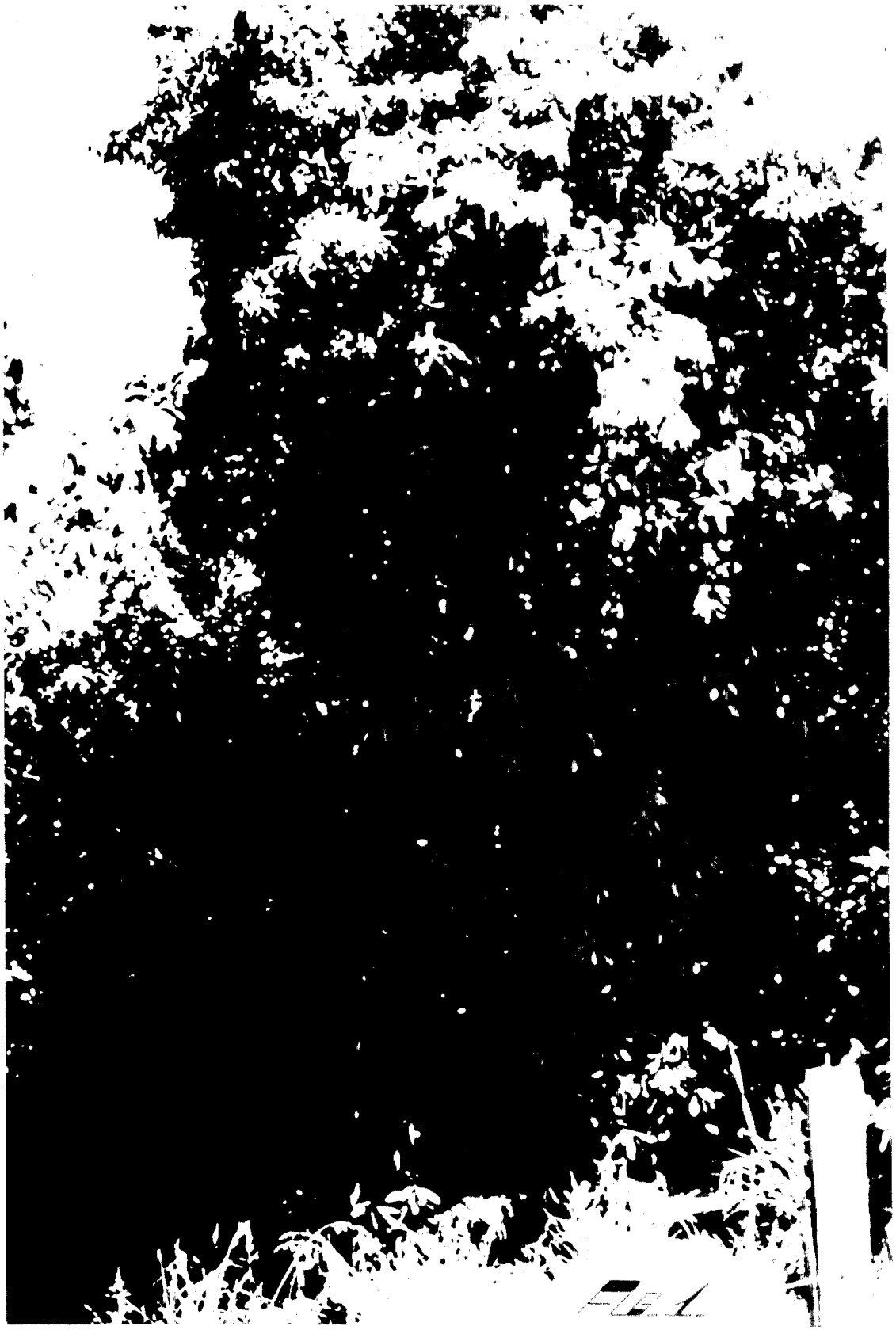
Figure 2:
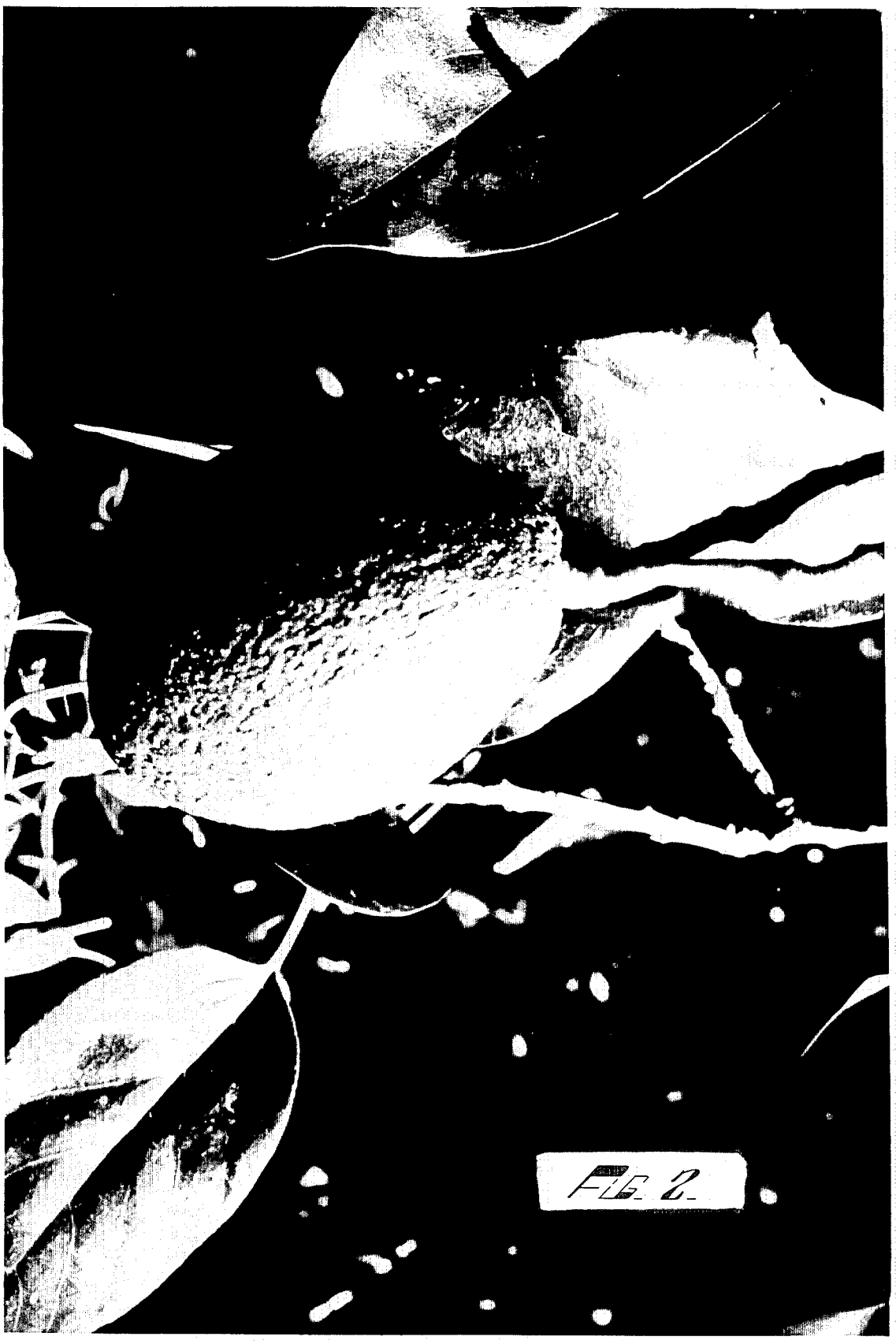
Figure 3:
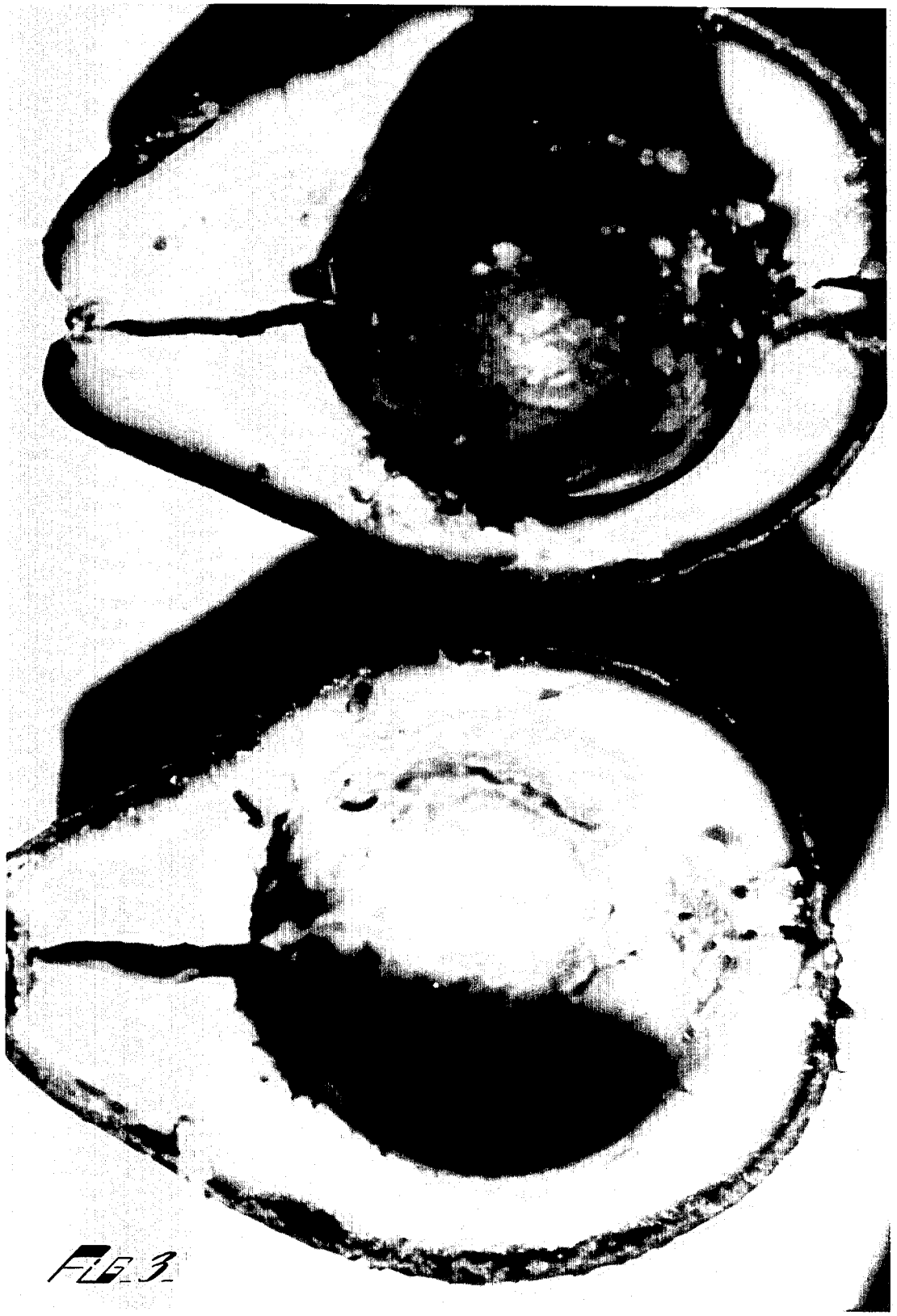
Figure 4:
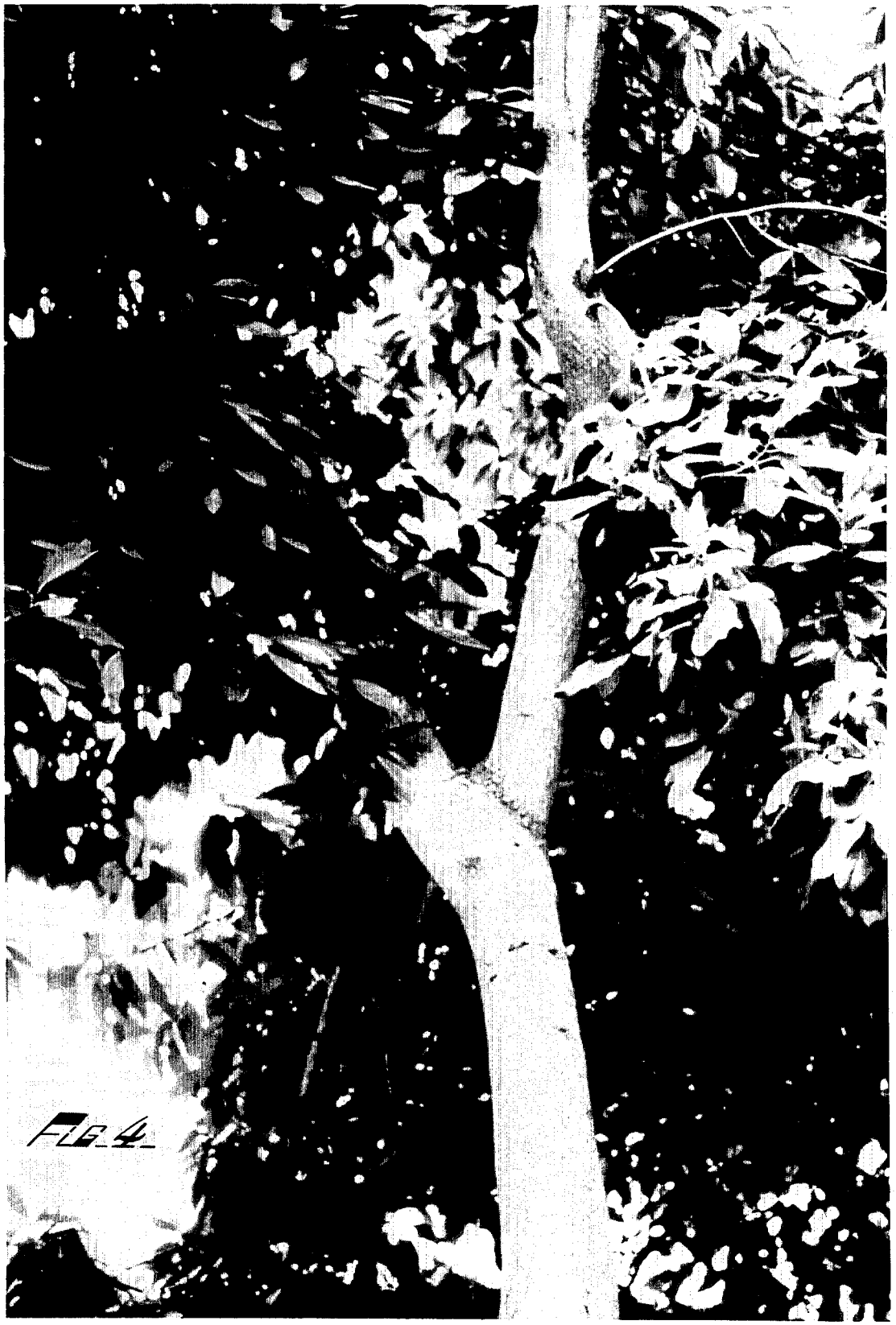

Other distinctive characteristics of the new variety are exemplified in the accompanying illustrations. FIG. 1 shows an entire tree. FIG. 2 shows a single whole fruit illustrating the exterior of the fruit and portions of the stem and leaves. FIG. 3 shows a transverse mid-section of the fruit illustrating the interior of the fruit. FIG. 4 shows the limited spreader characteristics of the tree.

TECHNICAL DESCRIPTION

The following is a brief description in some detail of the new variety of Avocado, color terminolgy being in accord with Maerz and Paul, *Dictionary of Color,* McGraw-Hill, 1950:

Tree:
- *Shape.*—Spherical, many lateral branches trunk to top.
- *Size.*—Medium; medium vigor; slightly upright, slightly spreading, height, slightly greater than width, minimal pruning.
- *Growth.*—Dense; branches have uniform distribution and width from trunk from top to bottom; well structured with conformity.
- *Trunk.*—Medium to slender with tendency of two or more main trunks.
- *Branches.*—Medium to slender; fairly smooth with scattered lenticels varying in size and shape.

Leaves:
- *Color of mature leaf.*—Danube green, plate 31, A-10.
- *Color of new leaf.*—Peacock green, Plate 20, C-9, not unlike Zutano.
- *Color of petiole.*—Light Yellowish-green, Plate 19, B-1.
- *Length.*—Variable up to seven inches.
- *Width.*—Variable up to three inches.
- *Shape.*—Long elliptical, pointed end, smooth edge in contrast to Zutano, very symmetrically shaped.
- *Aroma of leaves.*—Slightly licorice when crushed, assumption: Mexican variety.

Flower:
- *Size.*—Typical.
- *Season.*—Same as Zutano.
- *Cluster.*—Not quite as profuse as Zutano.

Fruit, external characters:
- *Color.*—Meadow green, Plate 30, D-10, quite like Fuerte.
- *Surface.*—Pebbly, more so than Fuerte.
- *Shape.*—Predominantly ovate, with some pear shaped. December maturity more pearshape, April to November very ovate-shaped, much like Haas.
- *Size.*—Variable; medium to large. Diameter axial 2.5 to 3.5 inches. Maximum transverse diameter 4 to 7 inches. Weight 8 to 12 ounces. Average fruit 8.5 to 10.5 ounces.
- *Base.*—Slightly umbilicate; oblique.
- *Apex.*—Broadly rounded.

*Stem.*—Length 3 to 4 inches, very thick, compared to Zutano.

*Skin.*—Thick, rough; as thick as or thicker than Haas.

Fruit, internal characters:

*Flesh color.*—Yellowish, Plate 17, D-1.

*Texture.*—Fine.

*Fibers.*—Few, fine.

*Ripens.*—Evenly, maturity season December 1st to September. San Joaquin Valley matures December 1st (one or two weeks after Zutano). Continues growth through August with test approaching 20% oil, holds 10 to 12 months on tree after December maturity. Skin turns darker approaching September with color much like Haas. Tree life and shelf life extremely long, more so than Haas.

*Flavor.*—Rich, very flavorful.

*Aroma.*—Slight.

Seed:

*Size.*—Small to medium, relative to size of fruit. Breadth $1\frac{1}{4}$ inches. Length $1\frac{1}{4}$ to $1\frac{1}{2}$ inches. Weight 35 to 40 grams for fruits weighing about 300 grams.

*Form.*—Broadly ovate, symmetrical. Base broadly rounded to flattened. Hilium broad. Apex obtuse. Sides equal.

*Surface.*—Pebbly.

*Color of seed surface.*—Light brown, Plate 8, H-1, seed coat adheres to seed, not at all to flesh.

Miscellaneous:

*Eating quality.*—Exceptional: nutty rich flavor more so than Haas or Fuerte. Inside flesh ripens uniformly. Six to eleven months after mature (hanging on tree) will be oily, skin so thick (yet easily separable) have to squeeze to note softness of flesh inside.

*Shipping qualities.*—Exceptional, as long as or longer shelf life than Haas.

*Yield.*—Medium to heavy. Parent tree non-alternate bearing.

*Oil content.*—From 8% in the month of December increasing as the year advances to 19% in the month of April to 22% in the month of October.

The above-described new variety of avocado tree has an unusually long harvest period with the ability to maintain fruit for long periods after maturity without affecting the quality of the fruit. The thick skin of the fruit provides for excellent shipping and shelf life qualities. In addition, and as can be appreciated from FIGS. 1 and 4, this new variety of tree exhibits both moderate maximum height and limited spreading characteristics, yielding dimensions which facilitate ease in harvesting.

I claim:

1. A new and distinct variety of avocado tree as described and illustrated, characterized particularly by its prolonged harvest period, the thick skin of the fruit, and limited height and limited spread of tree.

* * * * *